(12) United States Patent
Morita et al.

(10) Patent No.: US 10,045,786 B2
(45) Date of Patent: Aug. 14, 2018

(54) EXPANSILE MEMBER

(71) Applicant: MicroVention, Inc., Aliso Viejo, CA (US)

(72) Inventors: Hideo Morita, Irvine, CA (US); Greg Bak-Boychuk, San Clemente, CA (US); Arnold Tuason, Claremont, CA (US); Matthew J. Fitz, Vista, CA (US); George R. Greene, Jr., Costa Mesa, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 321 days.

(21) Appl. No.: 14/548,209

(22) Filed: Nov. 19, 2014

(65) Prior Publication Data

US 2015/0174381 A1 Jun. 25, 2015

Related U.S. Application Data

(60) Provisional application No. 61/919,651, filed on Dec. 20, 2013.

(51) Int. Cl.
| | |
|---|---|
| *A61M 29/04* | (2006.01) |
| *A61B 17/12* | (2006.01) |
| *A61M 25/00* | (2006.01) |
| *A61L 31/14* | (2006.01) |
| *A61B 17/00* | (2006.01) |

(52) U.S. Cl.
CPC .... *A61B 17/1219* (2013.01); *A61B 17/12113* (2013.01); *A61B 17/12172* (2013.01); *A61L 31/14* (2013.01); *A61L 31/145* (2013.01); *A61M 25/0082* (2013.01); *A61B 17/00491* (2013.01); *A61B 17/12186* (2013.01); *A61B 2017/00243* (2013.01); *A61B 2017/00575* (2013.01); *A61B 2017/00606* (2013.01); *A61B 2017/00623* (2013.01); *A61B 2017/00898* (2013.01); *A61B 2017/12054* (2013.01); *A61M 2025/0042* (2013.01); *A61M 2025/0096* (2013.01)

(58) Field of Classification Search
CPC .......... A61B 17/1219; A61B 17/12113; A61B 17/12172; A61B 17/12186; A61B 2017/00898; A61B 2017/12054; A61B 17/00491; A61B 2017/00243; A61B 2017/00575; A61B 2017/00606; A61B 2017/00623; A61L 31/14; A61L 31/145; A61M 25/0082; A61M 2025/0096
See application file for complete search history.

(56) References Cited

U.S. PATENT DOCUMENTS

| | | | | |
|---|---|---|---|---|
| 5,658,308 A * | 8/1997 | Snyder | ............. | A61B 17/12022 606/191 |
| 5,749,894 A * | 5/1998 | Engelson | ......... | A61B 17/12022 128/898 |
| 5,928,260 A * | 7/1999 | Chin | ................ | A61B 17/12022 604/107 |
| 6,036,720 A * | 3/2000 | Abrams | ........... | A61B 17/12022 606/200 |
| 6,296,657 B1 * | 10/2001 | Brucker | ............. | A61B 17/0057 606/192 |

(Continued)

*Primary Examiner* — Julian W Woo
(74) *Attorney, Agent, or Firm* — Inskeep IP Group, Inc.

(57) ABSTRACT

An expansile member that may be used on a delivery device or may be used for occlusive purposes within the vasculature.

10 Claims, 6 Drawing Sheets

(56) References Cited

U.S. PATENT DOCUMENTS

| | | | | |
|---|---|---|---|---|
| 6,723,108 B1* | 4/2004 | Jones | A61B 17/12022 | 606/151 |
| 7,942,894 B2* | 5/2011 | West | A61B 17/12022 | 294/99.1 |
| 8,273,100 B2* | 9/2012 | Martinez | A61B 17/12022 | 606/200 |
| 8,425,461 B2* | 4/2013 | Wilson | A61B 17/12022 | 604/113 |
| 8,597,320 B2* | 12/2013 | Sepetka | A61B 17/12022 | 606/200 |
| 9,724,103 B2* | 8/2017 | Cruise | A61B 17/12113 | |
| 9,795,389 B2* | 10/2017 | Elliott | A61B 17/12113 | |
| 2006/0106421 A1* | 5/2006 | Teoh | A61B 17/12022 | 606/213 |
| 2011/0257674 A1* | 10/2011 | Evert | A61B 17/12022 | 606/194 |

* cited by examiner

EXPANSILE MEMBER

RELATED APPLICATIONS

This application claims priority to U.S. Provisional Application Ser. No. 61/919,651 filed Dec. 20, 2013 entitled Expansile Member, which is hereby incorporated herein by reference in its entirety.

BACKGROUND OF THE INVENTION

Liquid embolic, which can be thought of as biocompatible glue, is often used in intravascular interventional procedures to embolize a site within the vasculature. Delivery of the liquid embolic can be difficult since the delivery device (i.e. catheter) may stick to the liquid embolic during delivery of said embolic. Additionally, potential backflow of the liquid embolic during delivery may cause embolic to migrate away from the treatment site. Reflux of the liquid embolic may cause the delivery device to stick to the embolic mass. An expansile member mounted to the delivery device would prevent these issues.

An expansile member could also be used as a treatment device to aid in various scenarios (i.e. aneurysms, atrial septal defects, patent foramen ovale, left atrial appendage occlusion, patent ductus arteriosis, fistula, arterio-venous malformations, occlusion in the peripheral vasculature) where space filling is required.

SUMMARY OF THE INVENTION

An expansile member is described.

In one embodiment an expansile member is connected to a retention member and mounted to a delivery device.

In another embodiment an expansile member is connected to a retention sleeve and mounted to a delivery device.

In another embodiment a catheter includes an expansile member connected to a retention member.

In another embodiment a catheter includes an expansile member connected to a retention sleeve.

In another embodiment an occlusive expansile member is described.

In another embodiment an occlusive expansile member for treating holes in the heart is described.

DESCRIPTION OF EMBODIMENTS

Figure 1:
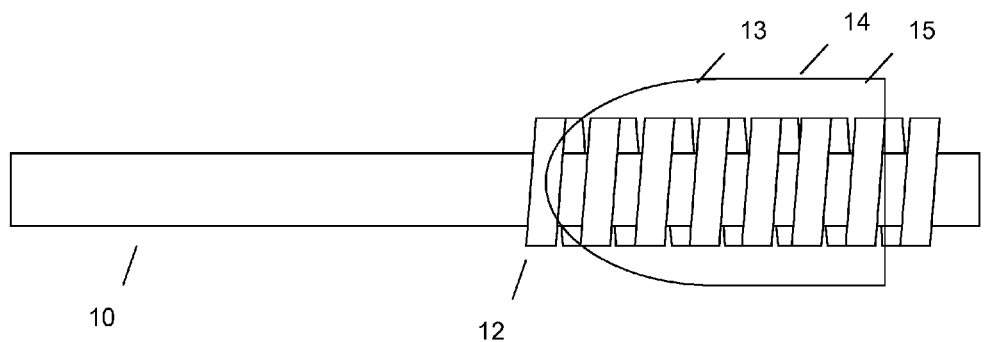
FIG. 1 is an elevation of an embodiment of an expansile member of the invention mounted to a delivery device.
Figure 2:
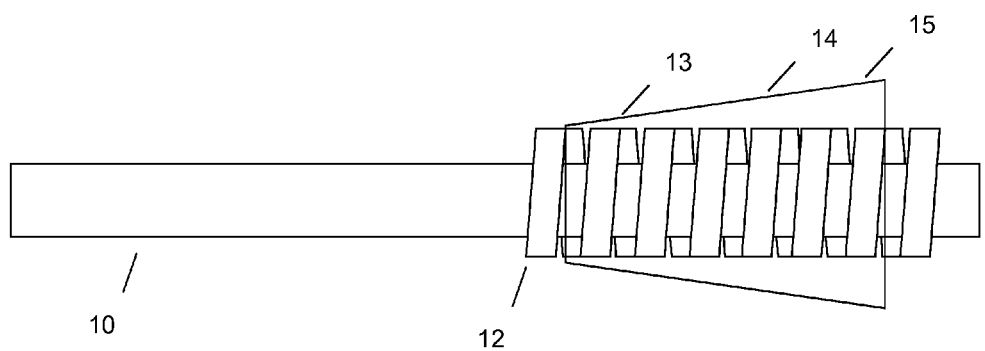
FIG. 2 is an elevation of an embodiment of an expansile member of the invention mounted to a delivery device.
Figure 3:
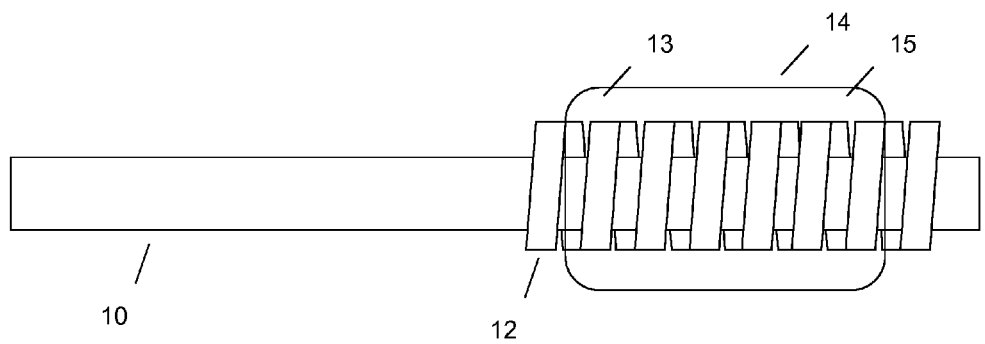
FIG. 3 is an elevation of an embodiment of an expansile member of the invention mounted to a delivery device.
Figure 4:
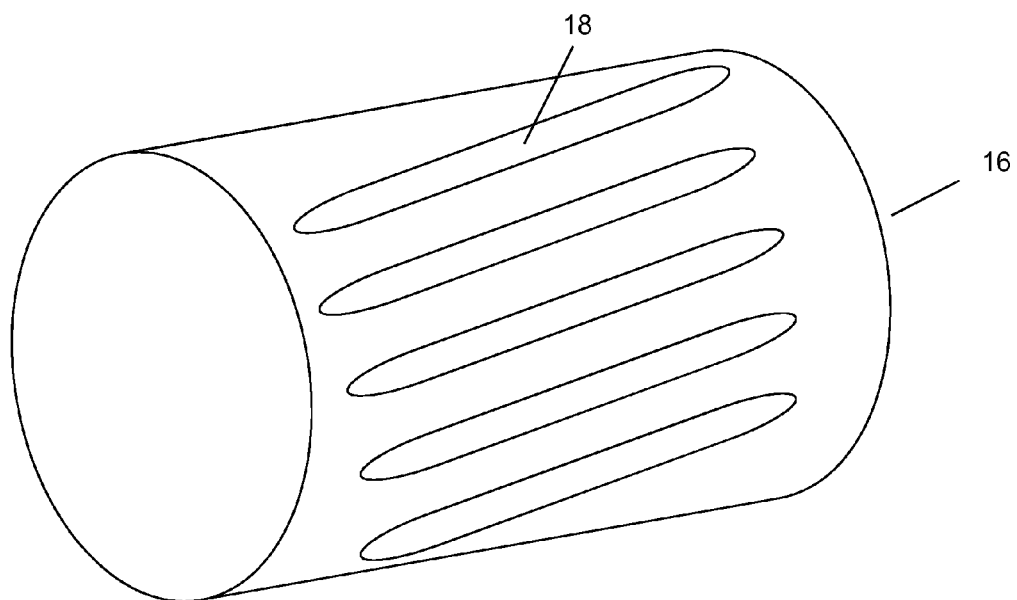
FIG. 4 is an elevation of an embodiment of a retention sleeve and an expansile member of the invention.
Figure 5:
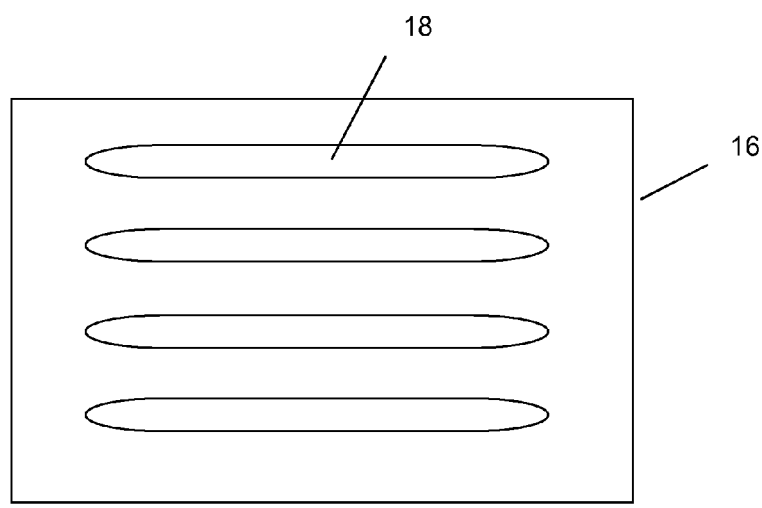
FIG. 5 is an elevation of an embodiment of a retention sleeve and an expansile member of the invention.

FIGS. 1-3 illustrate a delivery device 10 with an expansile member 14 and retention member 12 mounted on the delivery device 10. The delivery device 10 can be a catheter, hypotube, or other device used to deliver matter within the vasculature. In one example delivery device 10 is a microcatheter that may be used to deliver liquid embolic to a site within the vasculature.

The expansile member 14 is comprised of a hydrogel—an expansile, hydrophilic polymer. Hydrogels are often incorporated in embolization coils, where their expansile properties aid in space filling for applications such as aneurysm embolization. Hydrogels typically expand when exposed to material, such as blood. This response is based on the pH of the material to which the hydrogel is exposed. Thus, hydrogels utilized for intravascular procedures are designed to expand on contact with a substance having a pH within a pH range typical of blood.

Typically practitioners who regularly use liquid embolic materials encounter several problems. One problem is washout, which occurs when a high blood flow rate results in the liquid embolic getting washed away, especially in the opposite direction of the intended treatment site. One method of mitigating this problem is building up a dam of liquid embolic around the tip of the microcatheter. The inclusion of the expansile member 14 will eliminate the need for this dam since the expansile member 14 will fill the space between the microcatheter 10 and the vessel wall, thus preventing washout of the embolic and in effect acting as a dam.

Another problem is reflux of the embolic. As the clinician attempts to fill the treatment area (located distal of the distal tip of the delivery device), embolic may start to reflux proximally toward the distal tip of the catheter, especially as there is less resistance in this direction. Reflux may cause the catheter to get stuck to the embolic mass, in effect getting 'glued' into place. The expansile member 14 prevents reflux by filling the space around the distal tip of the delivery device thus blocking backflow.

FIGS. 1-3 show the expansile member 14 assuming a variety of shapes. Though only three are shown in these figures, namely ovular, frustoconical and cylindrical, respectively, it is to be understood that the expansile member 14 may assume a great variety of other shapes, including but not limited to circular, rectangular, non-symmetrical, polygonal, cubical, etc. Thus, the shapes shown are just examples of the various shapes said expansile member can assume. Each of the members 14 has a proximal end or portion 13 and a distal end or portion 15. The embodiments incorporating an unconstrained shape having increasing diameters, such as the frustocone of FIG. 2, are oriented such that the distal end 15 has a greater diameter than the proximal end 13.

Regardless of the unconstrained shape of the expansile member, it is desirable for the distal portion 13 of member 14 to expand to fill or substantially fill the gap between the delivery device and the wall of the vessel through which the delivery device is delivered. In the case where the microcatheter is used to deliver liquid embolic, the embolic is preferably delivered from the distal end of the microcatheter. The hydrogel may be configured to expand to its full diameter within 15-25 minutes, which should be sufficient time to advance the microcatheter to the target site based upon current clinical practices.

In a typical embolic procedure, a guide catheter is used to navigate a first portion of the vasculature. A guidewire is then used to navigate the remaining portion to the particular target location within the vasculature, and, finally, a microcatheter is delivered over this guidewire. The guidewire is subsequently withdrawn. Once the microcatheter is in place, liquid (or other) embolic is delivered through the microcatheter to treat the target site. Thus, the total microcatheter diameter (which includes the unexpanded expansile member mounted to a portion of the microcatheter) must be smaller than the inner diameter of the guide catheter in order to navigate through said guide catheter.

A retaining member is used to secure the expansile member 14 to the delivery device 10. In one example the retaining member is a coil 12 placed over the expansile member 14. Various coil properties can affect the expansile member 14. For example, a tightly wound coil or one with minimal gap length between windings will limit the amount of hydrogel that expands through the coil upon exposure to blood. A loosely wound coil or one with significant gap length between windings will allow more hydrogel expansion through said windings.

Various sizes can be used for all the elements (delivery device 10, expansile member 14, coil 12). One example configuration is as follows: the delivery device 10 is a microcatheter which has a 0.013" inner diameter and 0.021" outer diameter. The de-hydrated (pre-expanded) expansile member 14 has an inner diameter of 0.021" and a maximum outer diameter of 0.029' and is 0.09" long. The retaining member is a straight helical over-coil 12 with an inner diameter of 0.036", made from a 0.001" filar, and is 0.130" long. Note the expansile member 14 sits over the microcatheter 10, thus the inner diameter of the expansile member 14 matches the outer diameter of the microcatheter 10. The coil 12 is positioned over the expansile member 14 and both ends are pinched down onto the microcatheter body 10 with a coining tool, or via hand crimping. The pinched ends of the over-coil 12 may be secured to the microcatheter 10 via UV adhesive. The expansile member 14 may be secured to the microcatheter 10 with a UV adhesive and further restrained by the over-coil 12. In one example the over-coil 12 may be tensioned such that it sits into the unexpanded expansile member 14. In another example the over-coil 12 sits over or at the periphery of the unexpanded expansile member 14. The microcatheter 10 may be provided sterile with the incorporated ring and over-coil, and may include a hydrophilic coating to reduce friction when navigating the vasculature. In one example the expansile member 14 is not coated with a hydrophilic coating, said coating could delay expansion of the expansile member 14.

Figure 6:
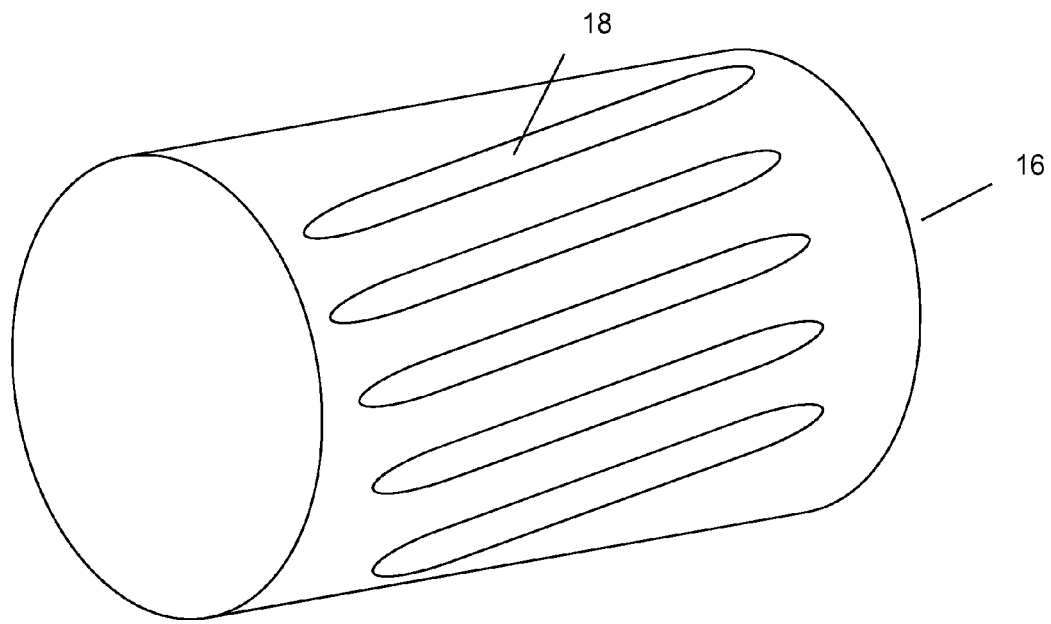
FIG. 6 is a perspective view of an embodiment of a retention sleeve and an expansile member of the invention.
Figure 7:
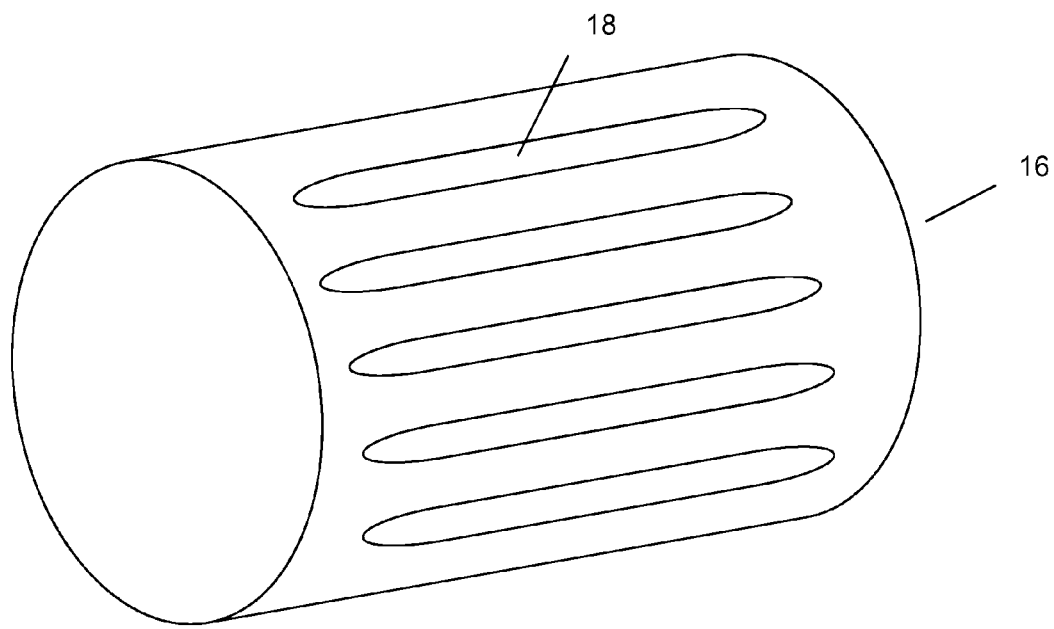
FIG. 7 is a perspective view of an embodiment of a retention sleeve and an expansile member of the invention.
Figure 8:
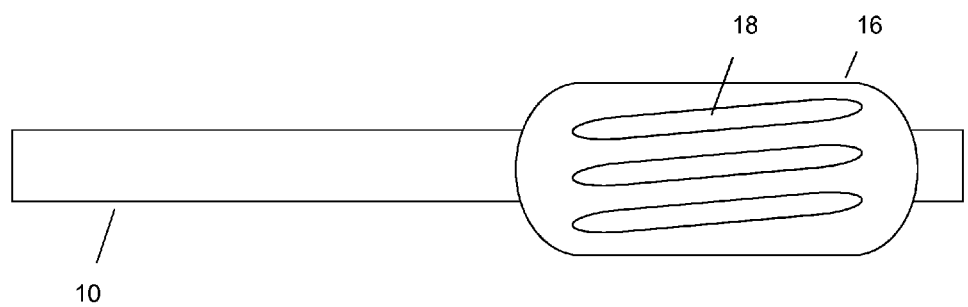
FIG. 8 is an elevation of an embodiment of an expansile member of the invention mounted to a delivery device.
Figure 9:
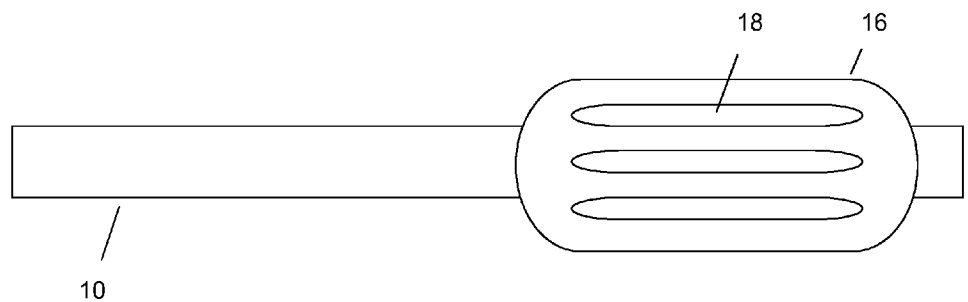
FIG. 9 is an elevation of an embodiment of an expansile member of the invention mounted to a delivery device.

FIGS. 4-9 illustrate another embodiment. In this embodiment instead of a coil 12, the retaining member is a retention sleeve 16, which physically sits over expansile member 14. The retention sleeve 16 is affixed to the microcatheter body 10 and acts like a cage for the expansile member 14 (not shown in FIGS. 4-9), which sits underneath the retention sleeve 16. The retention sleeve 16 includes one or more cells 18. These cells 18 can be thought of as open spaces in the sleeve 16. These cells 18 may be laser cut from sleeve 16. When expansile member 14 expands on contact with blood, it will expand through these cells 18. The cells 18 may take on any number of shapes including the ones shown in the Figures. Shapes as simple as slits, or complex geometric patterns can be used. In one example shown in FIGS. 4-5, the sleeve 16 is initially a plate with cells 18 inscribed from the plate. The plate can then be rolled into the sleeve shape shown in FIGS. 6-7. In another example the sleeve in FIGS. 6-7 is already formed and cells 18 are inscribed from the sleeve. The sleeve 16 can be made from an elastomeric material. The material should be sufficiently strong to pull the fully expanded hydrogel through a guide catheter, in the case where the guide catheter has a smaller diameter than the gels' fully expanded diameter. The over sizing of the expanded gel, in one example, can be as high as 50% greater than the guide catheter inner diameter. The material should also be compliant enough such that the caged gel is able to freely expand to the desired diameter. In one example Polyblend is used. In a more specific example Polyblend 1100 is used. In one example the cells 18 are configured such that the resulting shape of the expansile hydrogel member 14 has a shape similar to that of a football. The smaller diameter end regions of the football shape help lead the expanded gel back into the guide catheter during withdrawal of the device 10 while protecting the hydrogel from being sheared by the guide catheter orifice.

Retention sleeve 16 can be secured to the delivery device 10 (i.e. microcatheter) shaft by adhesive bonding, thermal fusion, or via mechanical means (i.e. retaining rings and/or marker bands).

Figure 10:
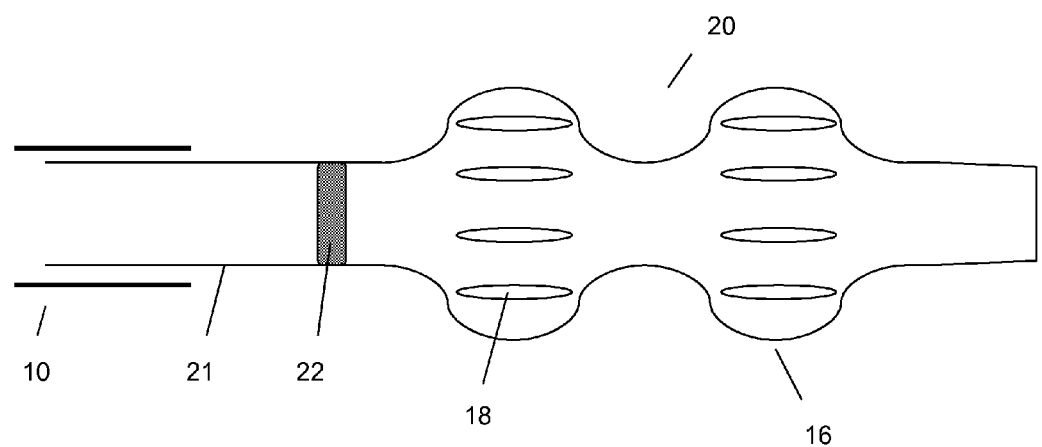
FIG. 10 is an elevation of an embodiment of an occlusive device of the invention; and, FIG. 11 is a depiction of an embodiment of an occlusive device of the invention delivered to a target location by an embodiment of a delivery device of the invention.

FIG. 10 illustrates another embodiment where an expansile member (not shown) is used in an occlusive device 20, where said device 20 is used for such purposes as occluding holes in a heart, more specifically holes in a baby's heart. The expansile member is used in a device 20, which has an undulating profile. An external sleeve 16, which has an undulating profile sits over an expansile member which sits underneath the sleeve. The sleeve 16 contains a number of cells 18. This sleeve 16 is similar to the retention sleeve 16 of FIGS. 8-9, just with a relatively more complex geometric shape than shown in those Figures. The expansile member, once exposed for a sufficient time to blood, will expand out of the cells 18. The narrow middle portion of occlusive device 20 sits physically at the hole in the heart while the wider portions immediately next to the middle portion would sit on either side of the hole to prevent blood from migrating through the hole. The expansion of the hydrogel expansile member will allow enhanced space filling around the hole, better preventing any blood seepage through the hole. In one example the sleeve functions as a hollow shell housing an expansile material (i.e. hydrogel), which fills the area within the shell. In another example the occlusive device contains an inner polymeric or metallic core, the expansile material sits around this inner core, and the shell sits around the expansile material. In this particular example, the amount of filler expansile material can be customized based on the thickness of this inner core. In another example utilizing either scenario just described, the expansile material (i.e. hydrogel), rather than filling the entire space underneath the shell, sits only immediately under the surface of the shell. Bonding means such as adhesive can be used to secure the expansile material to the inner surface of the shell.

The occlusive device 20 is delivered via a delivery device 10 (i.e. microcatheter) and can be connected to a pusher 21 with a detachment zone 22 which can be degraded or severed to detach the occlusive device 20 from pusher 21. Depending on the properties of sleeve 16 (i.e. restraining strength or thickness), the sleeve 16 may initially bulge out a bit when the expansile member starts to expand upon contact with blood, before the expansile member protrudes from cells 18. This bulging should not affect the overall shape of the occlusive device, as the occlusive device should have an undulating profile so the middle of the device bridges the hole while the proximal and distal bulged ends of the device 20 fill the space on either side of the hole.

Figure 11:
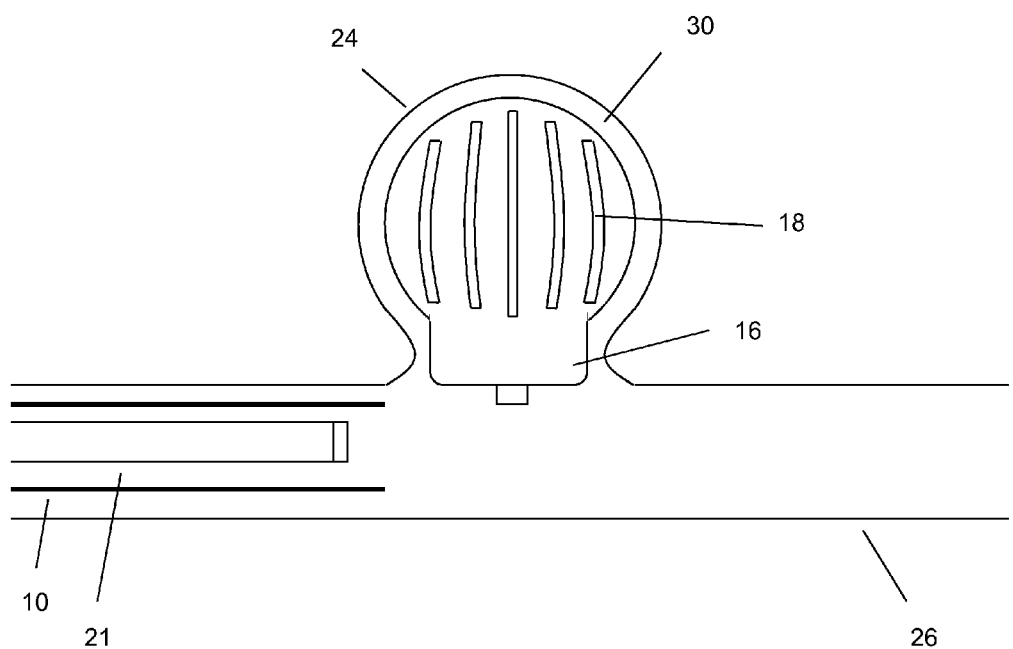

FIG. 11 illustrates another embodiment where an expansile member is used in an occlusive device 30, where said device is used for such purposes as aneurysm occlusion, left atrial appendage occlusion, vessel shut down, fistulas, or other vascular malformations where embolization is required. In FIG. 11 the occlusive device 30 is shown to occlude an aneurysm 24, where said aneurysm is a bulge in blood vessel 26. The occlusive device 30 is comprised of an external sleeve 16 that sits over an expansile member (not shown). This sleeve 16 is similar to the retention sleeve 16 of FIGS. 8-9, just with a relatively more complex geometric shape than shown in those Figures. The expansile member, once exposed for a sufficient time to blood, will expand out of cells 18. This will help to more thoroughly fill the malformation. In one example the sleeve 16 functions as a hollow shell housing an expansile material (i.e. hydrogel) which fills the area within the shell. In another example the occlusive device contains an inner polymeric or metallic core, the expansile material sits around this inner core, and the shell sits around the expansile material. In this particular example, the amount of filler expansile material can be customized based on the thickness of this inner core. In another example utilizing either scenario just described, the expansile material (i.e. hydrogel), rather than filling the entire space underneath the shell, sits only immediately under the surface of the shell. Bonding means such as adhesive can be used to secure the expansile material to the inner surface of the shell.

Depending on the properties of sleeve 16 (i.e. restraining strength or thickness), the sleeve may initially bulge out a bit when the expansile member starts to expand upon contact with blood, before the expansile member protrudes from cells 18. Device 30 is delivered via a pusher 21 and is delivered through a delivery device 10 (i.e. microcatheter). The pusher may contain a severable detachment zone linkage to sever the pusher from occlusive device 30.

The embodiments described in FIGS. 10-11 utilize a pusher with a severable and/or degradable detachment zone to deliver the occlusive device to the treatment site within the vasculature. Thermal, electrolytic, or mechanical means may be utilized to degrade this detachment zone, thus detaching the occlusive device from the pusher.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A system for delivering liquid embolic to a target site comprising:
    a liquid embolic;
    a microcatheter configured to deliver the liquid embolic;
    an expansile member disposed around an outside surface of a distal end of the microcatheter, wherein the expansile member is configured for insertion into the neck of an aneurysm and is substantially frustoconical, having an increasing diameter from a proximal end to a distal end in an expanded state;
    a coil securing the expansile member to the distal end of the microcatheter.

2. The system of claim 1 wherein the expansile member comprises a hydrogel.

3. The system of claim 1 wherein the coil has a diameter less than an expanded diameter of the expansile member.

4. A system for occluding blood flow in a vessel while delivering liquid embolic to a target site comprising:
    a microcatheter including a frustoconical expansile member at a distal end thereof and defining a lumen;
    a liquid embolic deliverable through said lumen; and,
    a retaining member surrounding the expansile member and containing slots through which the expansile member expands when assuming an expanded state, wherein in said expanded state, said expansile member has a diameter that decreases proximally, thereby allowing said expansile member to seat on an inside surface of an aneurysm neck.

5. The system of claim 4 wherein the expansile member comprises a hydrogel.

6. The system of claim 4 wherein the retaining member securing the expansile member to the distal end of the delivery device comprises a coil.

7. The system of claim 4 wherein the retaining member has a diameter less than an expanded diameter of the expansile member.

8. The system of claim 4 wherein the retaining member comprises a retention sleeve attached to the delivery device and at least partially containing the expansile member.

9. The system of claim 4 wherein said slots are arranged helically.

10. The system of claim 4 wherein said slots are arranged longitudinally.

* * * * *